United States Patent [19]

Grove

[11] 4,348,223

[45] Sep. 7, 1982

[54] N-ALKYL-N-[3-(ALKOXYALKYL)PHENYL]-2-HALOACETAMIDE HERBICIDES

[75] Inventor: William S. Grove, Doylestown, Ohio

[73] Assignee: PPG Industries, Inc., Pittsburgh, Pa.

[21] Appl. No.: 216,574

[22] Filed: Dec. 5, 1980

[51] Int. Cl.³ .................... A01N 37/22; C07C 103/32
[52] U.S. Cl. ........................................ 71/118; 564/214
[58] Field of Search .......................... 71/118; 564/214

[56] References Cited

U.S. PATENT DOCUMENTS

| | | | |
|---|---|---|---|
| 3,345,151 | 10/1967 | Olin | 71/118 |
| 3,547,620 | 12/1970 | Olin | 71/118 |
| 3,965,139 | 6/1976 | Scozzie | 260/465 D |
| 4,070,179 | 1/1978 | Vogel et al. | 260/562 B |

*Primary Examiner*—Catherine L. Mills
*Attorney, Agent, or Firm*—Edward J. Whitfield

[57] ABSTRACT

This invention concerns certain N-alkyl-N-[3-(alkoxyalkyl)phenyl]-2-haloacetamides having herbicidal activity, their preparation, and the control of weeds therewith.

5 Claims, No Drawings

N-ALKYL-N-[3-(ALKOXYALKYL)PHENYL]-2-HALOACETAMIDE HERBICIDES

FIELD OF THE INVENTION

This invention concerns certain N-alkyl-N-[3-(alkoxyalkyl)phenyl]-2-haloacetamides having herbicidal activity, their preparation, and the control of weeds therewith.

DESCRIPTION OF THE INVENTION

This invention concerns N-alkyl-N-[3-(alkoxyalkyl)phenyl]-2-haloacetamides represented by the formula:

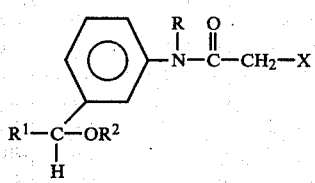

wherein:
R is alkyl containing up to 5 carbon atoms;
$R^1$ is hydrogen or alkyl containing up to 4 carbon atoms;
$R^2$ is alkyl containing up to 3 carbon atoms; and
X is halogen.

Exemplary of halogens represented by X in the above formula are bromine, chlorine, iodine, or fluorine, preferably bromine or chlorine. Some alkyl groups represented by the 'R' substituents are, for example, methyl, ethyl, n-propyl, isopropyl, n-butyl, sec-butyl, tert-butyl, n-pentyl, and the like.

Although any compound within the scope of the above formula is believed to have herbicidal activity in accordance with this invention, the compounds N-isopropyl-N-[3-(methoxymethyl)phenyl]-2-chloroacetamide, N-isopropyl-N-[3-(ethoxymethyl)phenyl]-2-chloroacetamide, N-isopropyl-N-[3-(isopropoxymethyl)phenyl]-2-chloroacetamide, N-isopropyl-N-[3-(1-methoxyeth-1-yl)phenyl]-2-chloroacetamide, N-sec-butyl-N-[3-(1-methoxyeth-1-yl)phenyl]-2-chloroacetamide and N-isopropyl-N-[3-(1-methoxyprop-1-yl)phenyl]-2-chloroacetamide have been found to be especially efficacious.

It is, of course, to be understood that the stereo and optical isomers of compounds represented by the above formula are within the scope of this invention.

The compounds of this invention are typically synthesized in a multi-stage process which involves reacting, in a first stage, appropriately substituted 3-nitrobenzyl halide with alkali metal alkoxide (or alcohol plus alkali metal hydroxide) to prepare 1-(alkoxyalkyl)-3-nitrobenzene of the formula:

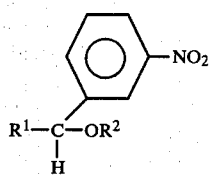

wherein $R^1$ and $R^2$ are as defined hereinabove. The 1-(alkoxyalkyl)-3-nitrobenzene is reduced to the corresponding aniline which is in turn reacted with an appropriately substituted ketone or aldehyde under reducing conditions to form the corresponding N-alkyl 3-(alkoxyalkyl)aniline of the formula:

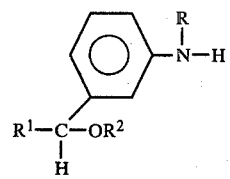

wherein R is as defined hereinabove. The N-alkyl 3-(alkoxyalkyl)aniline is, in the last stage, reacted with haloacetylhalide to form a compound of the invention.

An alternative mode of synthesis involves reacting, in the first stage, an appropriately substituted 3-nitrobenzyl alcohol with a dialkyl sulfoxide, e.g. dimethyl sulfoxide, to prepare the 1-(alkoxyalkyl)-3-nitrobenzene.

The starting materials used in the preparation of the compounds of this invention either may be obtained through commercial sources or synthesized by known techniques.

The following Examples are illustrative of the syntheses of certain N-alkyl-N-[3-(alkoxyalkyl)phenyl]-2-haloacetamides of the invention.

EXAMPLE I

Preparation of N-isopropyl-N-[3-(methoxymethyl)phenyl]-2-chloroacetamide (a) Preparation of 1-(methoxymethyl)-3-nitrobenzene A 500-milliliter flask equipped with a reflux condenser and a magnetic stirring bar was charged with 17.1 grams (0.1 mole) of 3-nitrobenzyl chloride in 200 milliliters of methanol. To this stirred solution was added 10.8 grams (0.2 mole) of sodium methoxide. Exothermic heating was observed. The reaction mixture was heated to reflux and maintained at reflux for 22 hours. The reaction mixture was then cooled, filtered, and the filtrate was transferred to a separatory funnel wherein it was diluted with 400 milliliters of ethyl acetate and consecutively extracted with 400 milliliters of water and 400 milliliters of saturated brine respectively. The organic phase was separated, dried over magnesium sulfate, and concentrated on a rotary evaporator at 55° C., leaving a brown liquid. The brown liquid was charged to a distillation flask and distilled at a pressure of 2.3 millimeters of mercury. A main fraction (15.1 grams) was collected, said fraction having a boiling point of 118°–120° C. at 2.3 mm Hg pressure. This main fraction was identified by NMR spectroscopy as 1-(methoxymethyl)-3-nitrobenzene.

(b) Preparation of 3-(methoxymethyl)aniline

A 300-cubic centimeter capacity stirred autoclave equipped with a heating mantle and sample port was charged with 15.03 grams (0.09 mole) of the 1-(methoxymethyl)-3-nitrobenzene prepared in paragraph (a) of this Example, and 0.75 gram of 5 percent platinum on carbon hydrogenation catalyst in 250 milliliters of ethyl acetate. The autoclave was then sealed, the air driven stirrer turned on, and the temperature was brought up to and maintained at about 90° C. The autoclave was then charged with hydrogen gas to a pressure of 200 psi (the valve to the hydrogen cylinder being left open). After 6 hours' reaction, the autoclave was cooled, broken open, and the contents were removed and filtered.

The filtrate was concentrated on a rotary evaporator at 55° C., leaving 12.3 grams of a yellow liquid identified by NMR spectroscopy as 3-(methoxymethyl)aniline.

(c) Preparation of N-isopropyl 3-(methoxymethyl)aniline

To the autoclave described in paragraph (b) was charged 2.74 grams (0.02 mole) of the 3-(methoxymethyl)aniline prepared in paragraph (b) of this Example and 0.6 gram of 5 percent platinum on carbon hydrogenation catalyst in 250 milliliters of anhydrous acetone. The autoclave was then sealed, the stirrer was turned on and the temperature was brought up to and maintained at about 90° C. The autoclave was charged with hydrogen gas to a pressure of 60 psi (the valve to the hydrogen cylinder being left open). After 23 hours the autoclave was cooled, broken open, and the contents removed and filtered. The filtrate was concentrated on a rotary evaporator at 55° C., leaving 3.4 grams of a clear liquid identified by NMR spectroscopy as N-isopropyl 3-(methoxymethyl)aniline.

(d) Preparation of N-isopropyl-N-[3-(methoxymethyl)phenyl]-2-chloroacetamide

A 3-necked, 100-milliliter flask provided with a reflux condenser, addition funnel, and magnetic stirring bar was charged with 3.04 grams (0.017 mole) of the N-isopropyl 3-(methoxymethyl)aniline prepared in paragraph (c) of this Example and 1.72 grams (0.017 mole) of triethylamine in 50 milliliters of benzene. To this stirred solution, at ambient temperature, was added dropwise 1.92 grams (0.017 mole) of chloroacetyl chloride. Exothermic heating was observed. The reaction mixture was brought to reflux and maintain at reflux for 5 hours. The reaction mixture was then cooled, transferred to a separatory funnel and washed consecutively with 30 milliliter portions each of 1 Normal hydrochloric acid, water, 1 Normal sodium hydroxide, and water. The organic phase was separated, dried over magnesium sulfate, and concentrated on a rotary evaporator at 55° C., yielding 3.8 grams of a light brown liquid identified by NMR spectroscopy as N-isopropyl-N-[3-(methoxymethyl)phenyl]-2-chloroacetamide having:

NMR (CDCl$_3$): 7–7.6$\delta$ (multiplet, 4H); 4.9$\delta$ (heptet, 1H); 4.45$\delta$ (singlet, 2H); 3.78$\delta$ (singlet, 2H); 3.38$\delta$ (singlet, 3H); and 1.08$\delta$ (doublet, 6H).

EXAMPLE II

Preparation of N-isopropyl-N-[3-(ethoxymethyl)phenyl]-2-chloroacetamide (a) Preparation of 1-(ethoxymethyl)-3-nitrobenzene A 300-milliliter flask equipped with a reflux condenser and a magnetic stirring bar was charged with 17.1 grams (0.1 mole) of 3-nitrobenzyl chloride in 150 milliliters of ethanol. To this stirred solution was added 6.8 grams (0.1 mole) of sodium ethoxide. The reaction mixture was heated to reflux and maintained at reflux for 21 hours. The reaction mixture was then cooled and concentrated on a rotary evaporator at 55° C. The residue was suspended in 250 milliliters of methylene chloride and transferred to a separatory funnel wherein it was washed consecutively with 100 milliliter portions of water, 1 Normal hydrochloric acid, water, 1 Normal sodium hydroxide, and water, respectively. The organic phase was separated, dried over magnesium sulfate, and concentrated on a rotary evaporator at 55° C., leaving a dark brown liquid. The dark brown liquid was charged to a distillation flask and distilled at a pressure of 2.0 millimeters of mercury. A main fraction (14 grams) was collected, said fraction having a boiling point of 112°–115° C. at 2 mm Hg pressure. This main fraction was identified by NMR spectroscopy as 1-(ethoxymethyl)-3-nitrobenzene.

(b) Preparation of 3-(ethoxymethyl)aniline

A 300-cubic centimeter capacity stirred autoclave equipped with a heating mantle and sample port was charged with 12.67 grams (0.07 mole) of the 1-(ethoxymethyl)-3-nitrobenzene prepared in paragraph (a) of this Example, and 0.8 gram of 5 percent platinum on carbon hydrogenation catalyst in 250 milliliters of ethyl acetate. The autoclave was then sealed, the air driven stirrer turned on, and the temperature was brought up to and maintained at about 80° C. The autoclave was then charged with hydrogen gas to a pressure of 200 psi (the valve to the hydrogen cylinder being left open). After 5 hours' reaction, the autoclave was cooled, broken open, and the contents were removed and filtered. The filtrate was concentrated on a rotary evaporator at 55° C., leaving 10.0 grams of a yellow liquid identified by NMR spectroscopy as 3-(ethoxymethyl)aniline.

(c) Preparation of N-isopropyl 3-(ethoxymethyl)aniline

To the autoclave described in paragraph (b) was charged 4.53 grams (0.03 mole) of the 3-(ethoxymethyl)aniline prepared in paragraph (b) of this Example and 0.5 gram of 5 percent platinum on carbon hydrogenation catalyst in 230 milliliters of anhydrous acetone. The autoclave was then sealed, the stirrer was turned on, and the temperature was brought up to and maintained at about 90° C. The autoclave was charged with hydrogen gas to a pressure of 100 psi (the valve to the hydrogen cylinder being left open). After 88 hours the autoclave was cooled, broken open, and the contents removed and filtered. The filtrate was concentrated on a rotary evaporator at 55° C., leaving 5.63 grams of a light brown liquid identified by NMR spectroscopy as N-isopropyl 3-(ethoxymethyl)aniline.

(d) Preparation of N-isopropyl-N-[3-(ethoxymethyl)phenyl]-2-chloroacetamide

A 3-necked, 100-milliliter flask provided with a reflux condenser, addition funnel, and magnetic stirring bar was charged with 1.93 grams (0.01 mole) of the N-isopropyl 3-(ethoxymethyl)aniline prepared in paragraph (c) of this Example and 1.01 grams (0.01 mole) of triethylamine in 50 milliliters of methylene chloride. To this stirred solution, at ambient temperature, was added dropwise 1.13 grams (0.01 mole) of chloroacetyl chloride. Exothermic heating was observed. The reaction mixture was brought to reflux and maintained at reflux for 47 hours. The reaction mixture was then cooled, transferred to a separatory funnel and washed consecutively with 30 milliliter portions each of 1 Normal hydrochloric acid, water, 1 Normal sodium hydroxide, and water, respectively. The organic phase was separated, dried over magnesium sulfate, and concentrated on a rotary evaporator at 55° C., yielding 2.13 grams of a light brown liquid identified by NMR spectroscopy as N-isopropyl-N-[3-(ethoxymethyl)phenyl]-2-chloroacetamide having:

NMR (CDCl$_3$): 6.25–7.1$\delta$ (multiplet, 4H); 4.35$\delta$ (singlet, 2H); 3.82$\delta$ (heptet, 1H); 3.45$\delta$ (quartet, 2H, singlet, 1H); and 1.15$\delta$ (multiplet, 9H).

EXAMPLE III

Preparation of
N-isopropyl-N-[3-(isopropoxymethyl)phenyl]-2-chloroacetamide (a) Preparation of 1-(isopropoxymethyl)-3-nitrobenzene A 500-milliliter flask equipped with a reflux condenser and a magnetic stirring bar was charged with 17.1 grams (0.1 mole) of 3-nitrobenzyl chloride in 250 milliliters of isopropanol. To this stirred solution was added 6.43 grams (0.1 mole) of potassium hydroxide in 25 milliliters of water. The reaction mixture was heated to reflux and maintained at reflux for 23 hours. The reaction mixture was then cooled, filtered, and the filtrate was concentrated on a rotary evaporator at 55° C. The residue was slurried with 300 milliliters of methylene chloride and transferred to a separatory funnel wherein it was washed consecutively with 100 milliliter portions of 1 Normal hydrochloric acid, water, 1 Normal sodium hydroxide, and water, respectively. The organic phase was separated, dried over magnesium sulfate, and concentrated on a rotary evaporator at 55° C., leaving a dark brown liquid. The dark brown liquid was charged to a distillation flask and distilled at a pressure of 2.4 millimeters of mercury. A main fraction (8.2 grams) was collected, said fraction having a boiling point of 123°–125° C. at 2.4 mm Hg pressure. This main fraction was identified by NMR spectroscopy as 1-(isopropoxymethyl)-3-nitrobenzene.

(b) Preparation of 3-(isopropoxymethyl)aniline

A 300-cubic centimeter capacity stirred autoclave equipped with a heating mantle and sample port was charged with 7.8 grams (0.04 mole) of the 1-(isopropoxymethyl)-3-nitrobenzene prepared in paragraph (a) of this Example, and 0.75 gram of 5 percent platinum on carbon hydrogenation catalyst in 230 milliliters of ethyl acetate. The autoclave was then sealed, the air driven stirrer turned on, and the temperature was brought up to and maintained at about 80° C. The autoclave was then charged with hydrogen gas to a pressure of 200 psi (the valve to the hydrogen cylinder being left open). After 5 hours' reaction, the autoclave was cooled, broken open, and the contents were removed and filtered. The filtrate was concentrated on a rotary evaporator at 55° C., leaving 5.98 grams of a light yellow liquid identified by NMR spectroscopy as 3-(isopropoxymethyl)aniline.

(c) Preparation of N-isopropyl 3-(isopropoxymethyl)aniline

To the autoclave described in paragraph (b) was charged 4.95 grams (0.03 mole) of the 3-(isopropoxymethyl)aniline prepared in paragraph (b) of this Example and 0.5 gram of 5 percent platinum on carbon hydrogenation catalyst in 230 milliliters of anhydrous acetone. The autoclave was then sealed, the stirrer was turned on, and the temperature was brought up to and maintained at about 90° C. The autoclave was charged with hydrogen gas to a pressure of 100 psi (the valve to the hydrogen cylinder being left open). After 25 hours the autoclave was cooled, broken open, and the contents removed and filtered. The filtrate was concentrated on a rotary evaporator at 55° C., leaving a brown liquid. NMR analysis indicated the brown liquid to be impure. Consequently, the brown liquid was purified by distillation at a pressure of 1.5 millimeters of mercury. A first cut (1.56 grams) was collected at 90° C. to 117° C., which also proved to be quite impure. A second substantially purer cut (1.15 grams) was collected at 118° C. to 122° C., which later was identified by NMR spectroscopy as N-isopropyl 3-(isoproxymethyl)aniline.

(d) Preparation of
N-isopropyl-N-[3-(isopropoxymethyl)phenyl]-2-chloroacetamide

A 3-necked, 100-milliliter flask provided with a reflux condenser, addition funnel, and magnetic stirring bar was charged with 1.03 grams (0.005 mole) of the N-isopropyl 3-(isopropoxymethyl)aniline prepared in paragraph (c) of this Example and 0.51 gram (0.005 mole) of triethylamine in 50 milliliters of methylene chloride. To this stirred solution, at ambient temperature, was added dropwise 0.57 gram (0.005 mole) of chloroacetyl chloride. Exothermic heating was observed. The reaction mixture was brought to reflux and maintained at reflux for 24 hours. The reaction mixture was then cooled, transferred to a separatory funnel and washed consecutively with 30 milliliter portions each of 1 Normal hydrochloric acid, water, 1 Normal sodium hydroxide, and water. The organic phase was separated, dried over magnesium sulfate, and concentrated on a rotary evaporator at 55° C., yielding 0.98 gram of a viscous, dark yellow liquid identified by NMR spectroscopy as N-isopropyl-N-[3-(isopropoxymethyl)phenyl]-2-chloroacetamide having:

NMR (CDCl$_3$): 6.85–7.65δ (multiplet, 4H); 4.92δ (heptet, 1H); 4.52δ (singlet, 2H); 3.7δ (singlet, 2H, overlapping a heptet, 1H); and 1.15δ (overlapping doublets, 12H).

EXAMPLE IV

Preparation of N-isopropyl-N-[3-(1-methoxyeth-1-yl)phenyl]-2-chloroacetamide (a) Preparation of 1-(1-methoxyeth-1-yl)-3-nitrobenzene A 1,000-milliliter flask equipped with a reflux condenser and a magnetic stirring bar was charged with 24.1 grams (0.13 mole) of α-methyl-3-nitrobenzyl chloride in 400 milliliters of methyl alcohol. To this stirred solution was added 8.1 grams (0.15 mole) of sodium methoxide. The reaction mixture was heated to reflux and maintained at reflux for 26 hours. Since some traces of α-methyl-3-nitrobenzyl chloride were present (as indicated by a thin layer chromatograph test), an additional 5.4 grams (0.1 mole) of sodium methoxide was added and the reaction was again heated to reflux and maintained at reflux for 49 hours. The reaction mixture was then cooled and concentrated on a rotary evaporator at 55° C. The residue was taken up with 200 milliliters of methylene chloride, transferred to a separatory funnel and washed consecutively with 100 milliliter portions each of water, 1 Normal hydrochloric acid, water, 1 Normal sodium hydroxide, and water, respectively. The organic layer was separated, dried over magnesium sulfate and concentrated on a rotary evaporator at 55° C., leaving a dark liquid residue. The dark liquid was charged to a distillation flask and distilled at a pressure of 1.8 millimeters of mercury. A main fraction (14.98 grams) was collected, said fraction having a boiling point of 106° C.–112° C. at 1.8 mm Hg pressure. This main fraction was identified by NMR spectroscopy as 1-(1-methoxyeth-1-yl)-3-nitrobenzene.

(b) Preparation of 3-(1-methoxyeth-1-yl)aniline

A 300-cubic centimeter capacity stirred autoclave equipped with a heating mantle and sample port was charged with 14.48 grams (0.08 mole) of the 1-(1-methoxyeth-1-yl)-3-nitrobenzene prepared in paragraph (a) of this Example, and 0.75 grams of 5 percent platinum on carbon hydrogenation catalyst in 220 milliliters of ethyl acetate. The autoclave was then sealed, the air driven stirrer turned on, and the temperature was brought up to and maintained at about 75° C. The autoclave was then charged with hydrogen gas to a pressure of 200 psi (the valve to the hydrogen cylinder being left open). After 5 hours' reaction, the autoclave was cooled, broken open, and the contents were removed and filtered. The filtrate was concentrated on a rotary evaporator at 55° C., leaving 11.87 grams of a light yellow liquid identified by NMR spectroscopy as 3-(1-methoxyeth-1-yl)aniline.

(c) Preparation of N-isopropyl 3-(1-methoxyeth-1-yl)aniline

To the autoclave described in paragraph (b) of this Example was charged 3.02 grams (0.02 mole) of the 3-(1-methoxyeth-1-yl)aniline prepared in paragraph (b) of this Example and 0.6 gram of 5 percent platinum on carbon hydrogenation catalyst in 230 milliliters of anhydrous acetone. The autoclave was then sealed, the stirrer was turned on, and the temperature was brought up to and maintained at about 70° C. The autoclave was charged with hydrogen gas and to a pressure of 150 psi (the valve to the hydrogen cylinder being left open). After 24 hours the autoclave was cooled, broken open, and the contents removed and filtered. The filtrate was concentrated on a rotary evaporator at 55° C., leaving 3.78 grams of a light orange liquid identified by NMR spectroscopy as N-isopropyl 3-(1-methoxyeth-1-yl)aniline.

(d) Preparation of N-isopropyl-N-[3-(1-methoxyeth-1-yl)phenyl]-2-chloroacetamide A 3-necked, 100-milliliter flask provided with a reflux condenser, addition funnel, and magnetic stirring bar was charged with 2.9 grams (0.015 mole) of the N-isopropyl 3-(1-methoxyeth-1-yl)aniline prepared in paragraph (c) of this Example and 1.52 grams (0.015 mole) of triethylamine in 50 milliliters of methylene chloride. To this stirred solution, at ambient temperature, was added dropwise 1.7 grams (0.015 mole) of chloroacetyl chloride. Exothermic heating was observed. The reaction mixture was brought to reflux and maintained at reflux for 45 hours. The reaction mixture was then cooled, transferred to a separatory funnel, and washed consecutively with 30 milliliter portions each of 1 Normal hydrochloric acid, water, 1 Normal sodium hydroxide, and water, respectively. The organic phase was separated, dried over magnesium sulfate, and concentrated on a rotary evaporator at 55° C., yielding 3.35 grams of an amber liquid identified by NMR spectroscopy as N-isopropyl-N-[3-(1-methoxyeth-1-yl)phenyl]-2-chloroacetamide having:

NMR (CDCl$_3$): 6.9–7.75$\delta$ (multiplet, 4H); 4.98$\delta$ (heptet, 1H); 4.33$\delta$ (quartet, 1H); 3.8$\delta$ (singlet, 2H); 3.23$\delta$ (singlet, 3H); 1.42$\delta$ (doublet, 3H); and 1.12$\delta$ (doublet, 6H).

EXAMPLE V

Preparation of N-sec-butyl-N-[3-(1-methoxyeth-1-yl)phenyl]-2-chloroacetamide (a) Preparation of N-sec-butyl 3-(1-methoxyeth-1-yl)aniline A 300-cubic centimeter capacity stirred autoclave equipped with a heating mantle and sample port was charged with 3.02 grams (0.02 mole) of the 3-(1-methoxyeth-1-yl)aniline prepared in paragraph (b) of Example IV and 0.6 gram of 5 percent platinum on carbon hydrogenation catalyst in 200 milliliters of methyl ethyl ketone. The autoclave was then sealed, the air driven stirrer turned on, and the temperature was brought up to and maintained at about 95° C. The autoclave was then charged with hydrogen gas to a pressure of 200 psi (the valve to the hydrogen cylinder being left open). After 5 hours' reaction, the autoclave was cooled, broken open, and the contents were removed and filtered. The filtrate was concentrated on a rotary evaporator at 55° C., leaving 11.87 grams of a light yellow liquid identified by NMR spectroscopy as N-sec-butyl-N-3-(1-methyleth-1-yl)aniline.

(b) Preparation of N-sec-butyl-N-[3-(1-methoxyeth-1-yl)phenyl]-2-chloroacetamide A 3-necked, 100-milliliter flask provided with a reflux condenser, addition funnel, and magnetic stirring bar was charged with 3.1 grams (0.015 mole) of the N-sec-butyl 3-(1-methoxyeth-1-yl)aniline prepared in paragraph (a) of this Example and 1.52 grams (0.015 mole) of triethylamine in 50 milliliters of benzene. To this stirred solution, at ambient temperature, was added dropwise 1.81 grams (0.016 mole) of chloroacetyl chloride. Exothermic heating was observed. The reaction mixture was brought to reflux and maintained at reflux for 6 hours. The reaction mixture was then cooled, transferred to a separatory funnel and washed consecutively with 30 milliliter portions each of 1 Normal hydrochloric acid, water, 5 percent aqueous sodium bicarbonate solution, and water, respectively. The organic phase was separated, dried over magnesium sulfate, and concentrated on a rotary evaporator at 55° C., yielding 3.5 grams of an amber liquid identified by NMR spectroscopy as N-sec-butyl-N-[3-(1-methoxyeth-1-yl)phenyl]-2-chloroacetamide having:

NMR (CDCl$_3$): 6.94–7.8$\delta$ (multiplet, 4H); 4.69$\delta$ (heptet, 1H); 4.38$\delta$ (quartet, 1H); 3.75$\delta$ (singlet, 2H); 3.25$\delta$ (singlet, 3H); and 0.81–1.69$\delta$ (multiplet, 11H).

EXAMPLE VI

Preparation of N-isopropyl-N-[3-(1-methoxyprop-1-yl)phenyl]-2-chloroacetamide (a) Preparation of 1-(1-methoxyprop-1-yl)-3-nitrobenzene A 500-milliliter flask equipped with a reflux condenser, an addition funnel and a magnetic stirring bar was charged with 31.6 grams (0.1749 mole) of α-ethyl-3-nitrobenzyl alcohol and 0.4 gram tetrabutylammonium iodide in 100 milliliters of diethyl ether. To this stirred mixture was added 36.4 grams (0.4546 mole) of 50 percent aqueous sodium hydroxide solution. Exothermic heating was observed. This mixture was vigorously stirred for 50 minutes, after which was added dropwise 26.6 grams (0.21 mole) of dimethyl sulfoxide. The mixture was stirred for 18 hours, after which an additional 2.0 grams of dimethyl sulfoxide was added and stirring continued for 2 hours. To this stirred mixture, 20 milliliters of concentrated ammonium hydroxide solution was carefully added and stirring continued for 1 hour. The mixture was then transferred to a separatory funnel, diluted with 100 milliliters of diethyl ether, thoroughly shaken, and the organic phase was withdrawn. The organic phase, after washing with 50 milliliters of water, was dried over magnesium sulfate and concentrated on a rotary evaporator at 55° C., leaving an amber liquid. The amber liquid was charged to a distillation flask and distilled at a pressure of 2.0 millimeters of mercury. A main fraction (21.0 grams) was collected, said fraction having a boiling point of 112° C.–115° C. at 2.0 mm Hg pressure. This main fraction was identified by NMR spectroscopy as 1-(1-methoxyprop-1-yl)-3-nitrobenzene.

(b) Preparation of 3-(1-methoxyprop-1-yl)aniline

A 300-cubic centimeter capacity stirred autoclave equipped with a heating mantle and sample port was charged with 19.5 grams (0.1 mole) of the 1-(1-methoxyprop-1-yl)-3-nitrobenzene prepared in paragraph (a) of this Example, and 0.75 gram of 5 percent platinum on carbon hydrogenation catalyst in 220 milliliters of ethyl acetate. The autoclave was then sealed, the air driven stirrer turned on, and the temperature was brought up to and maintained at about 70° C. The autoclave was then charged with hydrogen gas to a pressure of 200 psi (the valve to the hydrogen cylinder being left open). After 4 hours' reaction, the autoclave was cooled, broken open, and the contents were removed and filtered. The filtrate was concentrated on a rotary evaporator at 55° C., leaving 16.0 grams of a light green liquid identified by NMR spectroscopy as 3-(1-methoxyprop-1-yl)-aniline.

(c) Preparation of N-isopropyl 3-(1-methoxyprop-1-yl)aniline

To the autoclave described in paragraph (b) of this Example was charged 6.6 grams (0.04 mole) of the 3-(1-methoxyprop-1-yl)aniline prepared in paragraph (b) of this Example and 0.6 gram of 5 percent platinum on carbon hydrogenation catalyst in 230 milliliters of anhydrous acetone. The autoclave was then sealed, the stirrer was turned on, and the temperature was brought up to and maintained at about 70° C. The autoclave was charged with hydrogen gas to a pressure of 100 psi (the valve to the hydrogen cylinder being left open). After 19.5 hours the autoclave was cooled, broken open, and the contents removed and filtered. The filtrate was concentrated on a rotary evaporator at 55° C., leaving 7.8 grams of an amber liquid identified by NMR spectroscopy as N-isopropyl 3-(1-methoxyprop-1-yl)aniline.

(d) Preparation of N-isopropyl-N-[3-(1-methoxyprop-1-yl)phenyl]-2-chloroacetamide A 3-necked, 100-millilter flask provided with a reflux condenser, addition funnel, and magnetic stirring bar was charged with 2.07 grams (0.01 mole) of the N-isopropyl 3-(1-methoxyprop-1-yl)aniline prepared in paragraph (c) of this Example and 1.01 grams (0.01 mole) of triethylamine in 50 milliliters of methylene chloride. To this stirred solution, at ambient temperature, was added dropwise 1.14 grams (0.01 mole) of chloroacetyl chloride. Exothermic heating was observed. The reaction mixture was brought to reflux and maintained at reflux for 20 hours. The reaction mixture was then cooled, transferred to a separatory funnel and washed consecutively with 40 milliliter portions each of 1 Normal hydrochloric acid, water, 1 Normal sodium hydroxide, and water, respectively. The organic phase was separated, dried over magnesium sulfate, and concentrated on a rotary evaporator at 55° C., yielding 2.2 grams of an amber liquid identified by NMR spectroscopy as N-isopropyl-N-[3-(1-methoxy-prop-1-yl)phenyl]-2-chloroacetamide having:

NMR (CDCl$_3$): 7.08–7.65$\delta$ (multiplet, 4H); 4.95$\delta$ (heptet, 1H); 4.1$\delta$ (triplet, 1H); 3.7$\delta$ (singlet, 2H); 3.22$\delta$ (singlet, 3H); 1.7$\delta$ (quartet, 2H); and 0.7–1.2$\delta$ (multiplet, 9H).

The mode of synthesis of specific compounds of this invention has been illustrated in some detail by the foregoing Examples; but it is to be understood that any compound contemplated to be within the scope of this invention may be prepared by those skilled in the art simply by varying the choice of starting materials and using the illustrated techniques or other suitable techniques.

The compounds of this invention are effective in regulating the growth of a variety of undesirable plants, i.e. weeds, when applied, in an herbicidally effective amount, to the growth medium prior to emergence of the weeds or to the weeds subsequent to emergence from the growth medium. The term "herbicidally effective amount" is that amount of compound or mixture of compounds required to so injure or damage weeds such that the weeds are incapable of recovering following application. The quantity of a particular compound or mixture of compounds applied in order to exhibit a satisfactory herbicidal effect may vary over a wide range and depends on a variety of factors such as, for example, hardiness of a particular weed species, extent of weed infestation, climatic conditions, soil conditions, method of application, and the like. Typically, as little as 0.2 or less pound per acre to 10 or more pounds per acre of compound or mixtures of compounds may be reqquired. Of course, the efficacy of a particular compound against a particular weed species may readily be determined by relatively straightforward laboratory or field testing in a manner well known to the art.

The compounds of this invention may be used as such or in formulation with agronomically acceptable adjuvants, inert carriers, other herbicides, or other commonly used agricultural compounds, for example, pesticides, stabilizers, safeners, fertilizers, and the like. The compounds of this invention, whether or not in formulation with other agronomically acceptable materials, are typically applied in the form of dusts, granules, wettable powders, solutions, suspension, aerosols, emulsions, dispersions or the like in a manner well known to the art. When formulated with other typically used agronomically acceptable materials, the amount of compound or compounds of this invention present in the formulation may vary over a wide range, for example, from about 0.05 to about 95 percent by weight on weight of formulation. Typically such formulations will contain from about 5 to about 75 percent by weight of compound or compounds of this invention.

Certain of the compounds of this invention have been found effective in controlling a variety of broadleaf and grassy weeds at application rates ranging from two to ten pounds per acre preemergence while not significantly damaging desirable crops such as, for example, corn, cotton, soybeans, tomatoes, wheat, and rice. Exemplary of weeds that may be effectively controlled by the application of compounds of this invention are wild mustard (*Brassica kaber*); yellow foxtail (*Setaria glauca*); crabgrass (*Digitaria sanguinalis*); barnyardgrass (*Echinochloa crusgalli*); jimsonweed (*Datura stramonium*); teaweed (*Sida spinosa*); yellow nutsedge (*Cyperus esculentus*); and wild oats (*Avena fatua*).

The compounds prepared according to the Examples were tested for preemergence herbicidal activity against certain weed species under controlled laboratory conditions of light, temperature, and humidity.

The compounds were applied by spraying a solvent solution of the particular compound, at the desired rate of application, to shallow containers or flats containing the soil medium in which seeds of the selected weeds were sown. The state of growth of the weeds was observed and the toxic effect of each compound was periodically evaluated after application of the test compound.

The herbicidal effectiveness of a given compound or a given weed species is evaluated by visual inspection and by assigning a Numerical Injury Rating on a scale of from 0 (no injury) or 10 (all weeds dead). A rating of 8 or less indicates that a weed species may survive with the potential to reach maturity and produce seed, although a rating of at least 7, under competitive crop conditions, would constitute acceptable commercial weed control.

The following shows, in tabular form, the weed species (identified by column name) to which a test compound was applied (identified by reference to the Example in which the compound was prepared); the rate of application of the compound (in pounds per acre); the value of the Numerical Injury Rating of a particular compound against a particular weed species; and the number of days subsequent to application of the test compound when the Numerical Injury Rating was assigned.

| Weed Species | Compound | | | | |
| --- | --- | --- | --- | --- | --- |
| | I | II | III | IV | VI |
| Yellow nutsedge | 10 | 10 | — | 10 | — |
| Yellow foxtail | 9 | 10 | 10 | 10 | 10 |
| Large crabgrass | 9 | 10 | 7 | 10 | 9 |
| Wild oats | 8 | 9 | — | 8 | 7 |
| Barnyardgrass | 10 | 7 | 10 | 10 | 10 |
| Teaweed | 10 | 8 | — | — | 8 |

-continued

| Weed Species | Compound | | | | |
| --- | --- | --- | --- | --- | --- |
| | I | II | III | IV | VI |
| Jimsonweed | 10 | — | — | — | — |
| Wild Mustard | 10 | — | — | — | — |
| Rate, lb/A | 5 | 10 | 5 | 2 | 10 |
| Days | 21 | 21 | 22 | 21 | 23 |

Although the invention has been described in considerable detail with reference to illustrative embodiments thereof, it is to be understood that it is not intended to be so limited without departing from the spirit and scope thereof, except as defined by the appended claims.

I claim:

1. A compound represented by the formula:

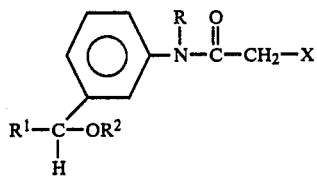

wherein:
R is alkyl containing up to 5 carbon atoms;
$R^1$ is hydrogen or alkyl containing up to 4 carbon atoms;
$R^2$ is alkyl containing up to 3 carbon atoms; and
X is halogen.

2. A compound of claim 1 wherein X is chlorine or bromine.

3. A compound of claim 1 selected from N-isopropyl-N-[3-(methoxymethyl)phenyl]-2-chloroacetamide, N-isopropyl-N-[3-(ethoxymethyl)-phenyl]-2-chloroacetamide, N-isopropyl-N-[3-(isopropoxymethyl)phenyl]-2-chloroacetamide, N-isopropyl-N-[3-(1-methoxyeth-1-yl)phenyl]-2-chloroacetamide, N-sec-butyl-N-[3-(1-methoxyeth-1-yl)phenyl]-2-chloroacetamide, or N-isopropyl-N-[3-(1-methoxyprop-1-yl)phenyl]-2-chloroacetamide.

4. A herbicidal composition containing a herbicidally effective amount of a compound or mixture of compounds defined by claim 1.

5. In a method of controlling weed growth wherein a herbicidally effective amount of a herbicide is either applied to a growth medium prior to emergence of weeds therefrom or is applied to the weeds subsequent to their emergence from the growth medium wherein the improvement resides in using as the herbicide a herbicidally effective amount of a compound or mixture of compounds defined in claim 1.

* * * * *